(12) United States Patent
Provitera

(10) Patent No.: US 9,346,571 B2
(45) Date of Patent: May 24, 2016

(54) MULTI-CHAMBER FREEZING BAG

(71) Applicant: Pall Corporation, Port Washington, NY (US)

(72) Inventor: Paxton E. Provitera, East Meadow, NY (US)

(73) Assignee: Pall Corporation, Port Washington, NY (US)

( * ) Notice: Subject to any disclaimer, the term of this patent is extended or adjusted under 35 U.S.C. 154(b) by 475 days.

(21) Appl. No.: 14/068,186

(22) Filed: Oct. 31, 2013

(65) Prior Publication Data

US 2015/0113919 A1    Apr. 30, 2015

(51) Int. Cl.

| | |
|---|---|
| *A61J 1/05* | (2006.01) |
| *A61J 1/14* | (2006.01) |
| *B65B 31/00* | (2006.01) |
| *B65B 55/00* | (2006.01) |
| *B65B 63/08* | (2006.01) |
| *B65B 7/02* | (2006.01) |
| *B29C 65/78* | (2006.01) |
| *B29C 65/00* | (2006.01) |
| *B29C 65/02* | (2006.01) |
| *A61J 1/16* | (2006.01) |
| *A61M 1/02* | (2006.01) |
| *A61J 1/10* | (2006.01) |
| *A01N 1/02* | (2006.01) |

(Continued)

(52) U.S. Cl.
CPC ............... *B65B 7/02* (2013.01); *A01N 1/0263* (2013.01); *A01N 1/0268* (2013.01); *A61J 1/165* (2013.01); *A61M 1/0209* (2013.01); *B29C 65/02* (2013.01); *B29C 65/7841* (2013.01); *B29C 66/1122* (2013.01); *B29C 66/4312* (2013.01); *B29C 66/73921* (2013.01); *B29C 66/8491* (2013.01); *A01N 1/0284* (2013.01); *A61J 1/10* (2013.01); *A61M 1/0272* (2013.01); *A61M 1/0277* (2014.02); *A61M 1/0281* (2013.01); *A61M 2207/00* (2013.01); *B29C 65/18* (2013.01); *B29C 66/43121* (2013.01); *B29C 66/71* (2013.01); *B29C 66/7373* (2013.01); *B29C 66/8324* (2013.01); *B29C 66/83221* (2013.01); *B29L 2031/7148* (2013.01)

(58) Field of Classification Search
CPC .............. A01N 1/0263; A61M 1/0209; A61M 1/0272; A61M 1/0277; A61M 1/0281; F25D 2331/8014; A61J 1/10; B29C 65/78; B29C 65/02; B65B 2230/02
USPC ............... 53/111 R, 170, 173, 428, 440, 476; 206/471, 524.1, 524.4, 569; 604/403, 604/408–411, 317
See application file for complete search history.

(56) References Cited

U.S. PATENT DOCUMENTS

| | | |
|---|---|---|
| 2,736,277 A | 2/1956 | Cole, Jr. |
| 3,776,411 A | 12/1973 | Luckadoo |
| 4,090,374 A | 5/1978 | Faust et al. |

(Continued)

FOREIGN PATENT DOCUMENTS

| | | |
|---|---|---|
| EP | 0770838 A1 | 5/1997 |
| WO | WO 95/09597 A1 | 4/1995 |

(Continued)

*Primary Examiner* — Stephen F Gerrity
*Assistant Examiner* — Eyamindae Jallow
(74) *Attorney, Agent, or Firm* — Jeremy Jay

(57) ABSTRACT

Methods for preparing and using multiple chambered freezing bags containing biological fluid in the chambers are disclosed.

8 Claims, 2 Drawing Sheets

(51) Int. Cl.
  *B29C 65/18* (2006.01)
  *B29L 31/00* (2006.01)

(56) References Cited

U.S. PATENT DOCUMENTS

| | | | | |
|---|---|---|---|---|
| 4,194,369 A | * | 3/1980 | Faust | F25D 3/10 |
| | | | | 206/438 |
| 5,415,282 A | * | 5/1995 | Kienholz | A01N 1/02 |
| | | | | 206/216 |
| 5,935,848 A | | 8/1999 | Sputtek et al. | |
| 6,213,334 B1 | | 4/2001 | Coelho et al. | |
| 6,378,314 B1 | * | 4/2002 | Clark | F17C 3/10 |
| | | | | 62/457.9 |
| 6,426,035 B1 | | 7/2002 | Hansen | |
| 8,177,123 B2 | | 5/2012 | Voute et al. | |
| 8,287,680 B2 | | 10/2012 | Foucaut et al. | |
| 2007/0257039 A1 | | 11/2007 | Chammas | |
| 2008/0103428 A1 | * | 5/2008 | Delaronde-Wilton | A61M 1/0209 |
| | | | | 604/6.03 |
| 2009/0158755 A1 | * | 6/2009 | Cutting | A01N 1/02 |
| | | | | 62/66 |
| 2010/0072216 A1 | * | 3/2010 | Voute | A01N 1/0263 |
| | | | | 220/737 |
| 2012/0184033 A1 | | 7/2012 | Crimmins et al. | |
| 2013/0018353 A1 | | 1/2013 | Chung et al. | |

FOREIGN PATENT DOCUMENTS

| | | |
|---|---|---|
| WO | WO 99/28204 A1 | 6/1999 |
| WO | WO 02/38200 | 5/2002 |
| WO | WO 2006/027565 A1 | 3/2006 |
| WO | WO 2009/138966 A2 | 11/2009 |
| WO | WO 2010/129569 A1 | 11/2010 |

* cited by examiner

MULTI-CHAMBER FREEZING BAG

BACKGROUND OF THE INVENTION

Blood components such as plasma, red blood cells, leukocytes, stem cells and progenitor cells can be frozen for long term storage at cryogenic temperatures, using single chamber freezing bags, or dual chamber freezing bags wherein the chambers have different volumes.

However, there is a need for improved methods for preparing multiple chamber freezing bags.

The present invention provides for ameliorating at least some of the disadvantages of the prior art. These and other advantages of the present invention will be apparent from the description as set forth below.

BRIEF SUMMARY OF THE INVENTION

An embodiment of the invention provides a method for sealing a freezable bag having multiple compartments containing biological fluid, the method comprising inserting a freezable bag comprising opposing side walls having exterior surfaces, a top, and a bottom, and multiple compartments, each compartment having an interior volume containing biological fluid therein, the bag further comprising a passageway providing fluid communication between the compartments, between first and second panels of an open jig, the first and second panels each having an outside surface and an inside surface, the inside surfaces forming an interior of the jig, the first and second panels each having a plurality of cut outs at one end of the panels; closing the jig with the bag located in the interior of the jig, such that the inside surfaces of the first and second panels contact the exterior surfaces of the opposing side walls of the bag; applying heat to the bag through the plurality of cut outs; and sealing the passageway and forming a plurality of sealed fluidly isolated biological fluid containing compartments in the bag, each compartment containing about the same volume of biological fluid.

BRIEF DESCRIPTION OF THE SEVERAL VIEWS OF THE DRAWING(S)

FIG. 1 shows a 5 chamber freezing bag suitable for use in an embodiment of a method of the present invention.

DETAILED DESCRIPTION OF THE INVENTION

Figures 1A, 1B:
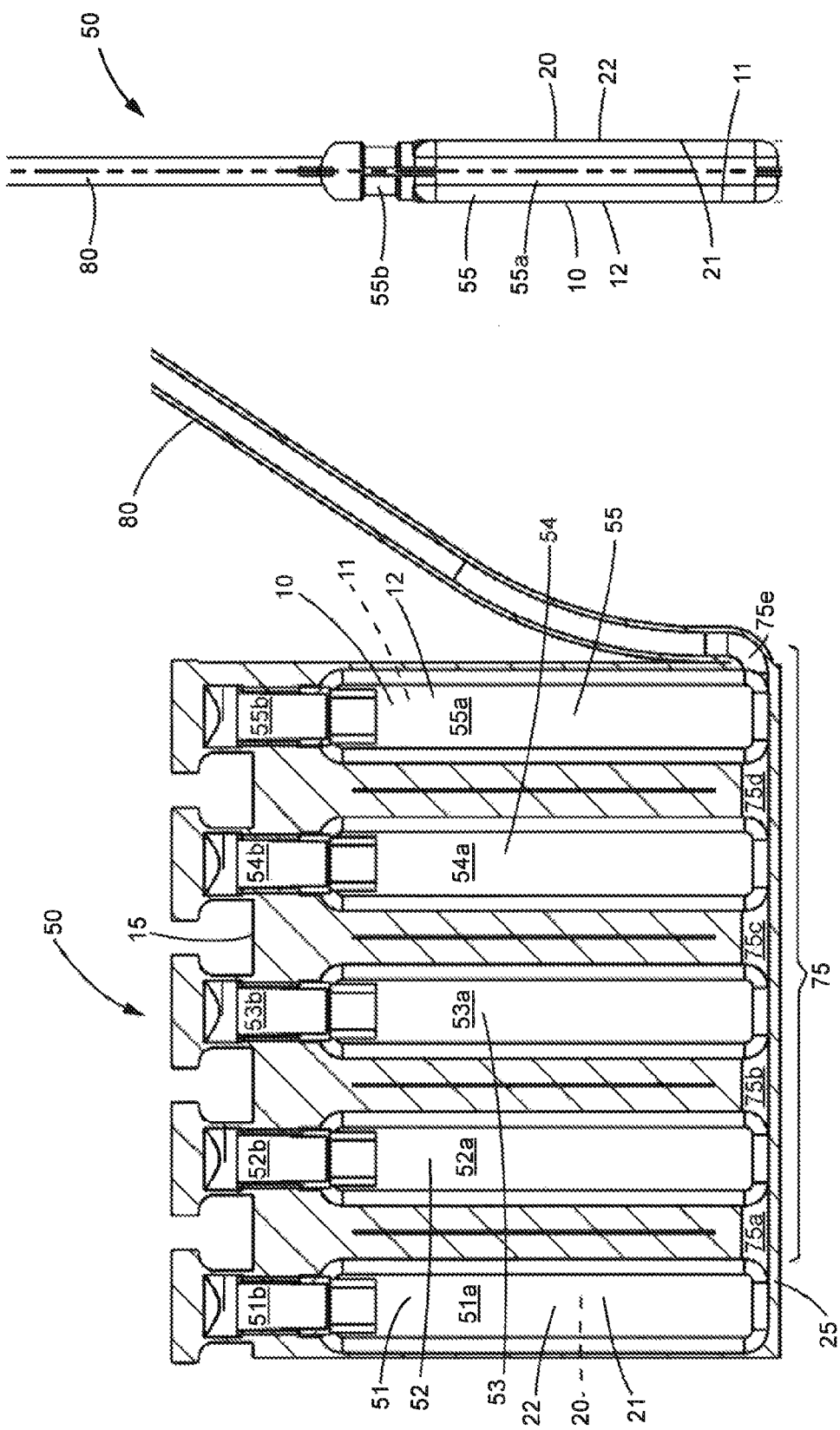
FIG. 1A shows a front view.
FIG. 1B shows a side view.

In accordance with an embodiment of the present invention, a method for sealing a freezing bag having multiple compartments containing biological fluid is provided, the method comprising (a) inserting a freezing bag comprising opposing side walls having exterior surfaces, a top, and a bottom, and multiple compartments, each compartment having an interior volume containing biological fluid therein, the bag further comprising a passageway providing fluid communication between the compartments, between first and second panels of an open jig, the first and second panels each having an outside surface and an inside surface, the inside surfaces forming an interior of the jig, the first and second panels each having a plurality of cut outs at one end of the panels; (b) closing the jig with the bag located in the interior of the jig, such that the inside surfaces of the first and second panels contact the exterior surfaces of the opposing side walls of the bag; (c) applying heat to the bag through the plurality of cut outs; and (d) sealing the passageway and forming a plurality of sealed fluidly isolated biological fluid containing compartments in the bag, each compartment containing about the same volume of biological fluid.

In some embodiments, the panels are connected by a hinge, and closing the jig comprises pivoting one of the first or second panels toward the other of the first or second panels.

In a preferred embodiment, the method comprises forming at least 3 sealed fluidly isolated biological fluid containing compartments in the bag, each compartment containing about the same volume of biological fluid.

Embodiments of the method can further comprise freezing the freezing bag comprising the plurality of sealed fluidly isolated biological fluid containing compartments.

Advantageously, a number of samples having high concentrations of cells in small volumes can be frozen and stored long term in a single bag while reducing space usage. When the samples are derived from one donor, one sample can be used while keeping the other samples in safe sterile storage for potential use.

The following definitions are used in accordance with the invention.

Biological Fluid. A biological fluid includes any treated or untreated fluid associated with living organisms, particularly blood, including whole blood, warm or cold blood, cord blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); blood products derived from blood or a blood component or derived from bone marrow; stem cells; red cells separated from plasma and resuspended in a physiological solution or a cryoprotective fluid; and platelets separated from plasma and resuspended in a physiological solution or a cryoprotective fluid. A biological fluid also includes a physiological solution comprising a bone marrow aspirate. The biological fluid may have been treated to remove some of the leukocytes before being processed according to the invention. As used herein, blood product or biological fluid refers to the components described above, and to similar blood products or biological fluids obtained by other means and with similar properties.

In some embodiments, the freezing bags (which are preferably flexible bags) further comprise conduits and/or entry ports such as spike entry ports. In one embodiment, the bags are suitable for use while maintaining a closed system. Preferably, the bags (as well as conduits and entry ports) are made from materials having low glass transition temperatures, for withstanding cryogenic temperatures, and suitable materials are known in the art. For example, freezing bags (and conduits and/or entry ports) can be made from plasticized polyvinyl chloride, ethylene butyl acrylate copolymer (EBAC) resin, ethylene methyl acrylate copolymer (EMAC) resin, plasticized ultra-high-molecular weight PVC resin, and ethylene vinyl acetate (EVA). The bags (and conduits and/or entry ports) can also be formed from, for example, polyethylene, polyolefin, polypropylene, polyurethane, polyester, fluoropolymers, and polycarbonate and combinations of materials. Suitable freezable bags can be prepared by methods known in the art, and a variety of suitable conduits and entry ports are known in the art.

In those embodiments including cryopreservation of the desired biological fluid components (e.g., red blood cells, leukocytes, progenitor cells and/or stem cells), the chambers typically contain, in addition to the biological fluid, cryopreservatives such as dimethyl sulfoxide (DMSO), and/or other cryopreservatives compatible with cryopreservation, including, but are not limited to, those disclosed in U.S. Pat. Nos. 6,146,124, and 5,789,147, U.S. Patent Application Publication 2004/0254560, and Canadian Patent Application 2259878.

As used herein, the term "closed" refers to a system that allows the collection and processing (and, if desired, the manipulation, e.g., separation of portions, separation into components, filtration, storage, and preservation) of biological fluid, e.g., donor blood, blood samples, and/or blood components, without the need to compromise the sterile integrity of the system. A closed system can be as originally made, or result from the connection of system components using what are known as "sterile docking" devices. Illustrative sterile docking devices are disclosed in, for example, U.S. Pat. Nos. 4,507,119, 4,737,214, and 4,913,756.

Each of the components of the invention will now be described in more detail below, wherein like components have, like reference numbers.

The freezing bag has opposing side walls having exterior surfaces and interior surfaces, a top, and a bottom, and defining an interior volume and containing biological fluid in the interior volume. Embodiments of the invention are suitable for use with freezing bags having two or more chambers, preferably, three or more chambers, more preferably, at least five chambers.

The illustrative freezing bag 50 shown in FIG. 1 is a multiple chamber freezing bag suitable for use in an embodiment of a method of the present invention, wherein the bag has opposing side walls 10 and 20, side wall 10 having an interior surface 11 and an exterior surface 12, and side wall 20 having an interior surface 21 and an exterior surface 22. The bag has a top end 15 and a bottom end 25. The illustrated bag comprises 5 chambers (51, 52, 53, 54, 55), each having an interior volume (51a, 52a, 53a, 54a, 55a, respectively, formed by portions of the interior surfaces 11 and 21 where they are not sealed together) containing biological fluid therein. Each chamber communicates with an outlet port (51b, 52b, 53b, 54b, 55b, respectively (illustrated as spike entry ports). Before sealing in accordance with the invention, a pathway 75 provides fluid communication to and between the chambers (via 75a, 75b, 75c, 75d, and 75e), the pathway communicating with fill line tubing 80. With the exception of the pathway 75, the chambers are peripherally sealed such that there is no fluid communication between each other, and the chambers are sealed at their ends opposite the pathway 75 via the outlet ports.

Figure 2:
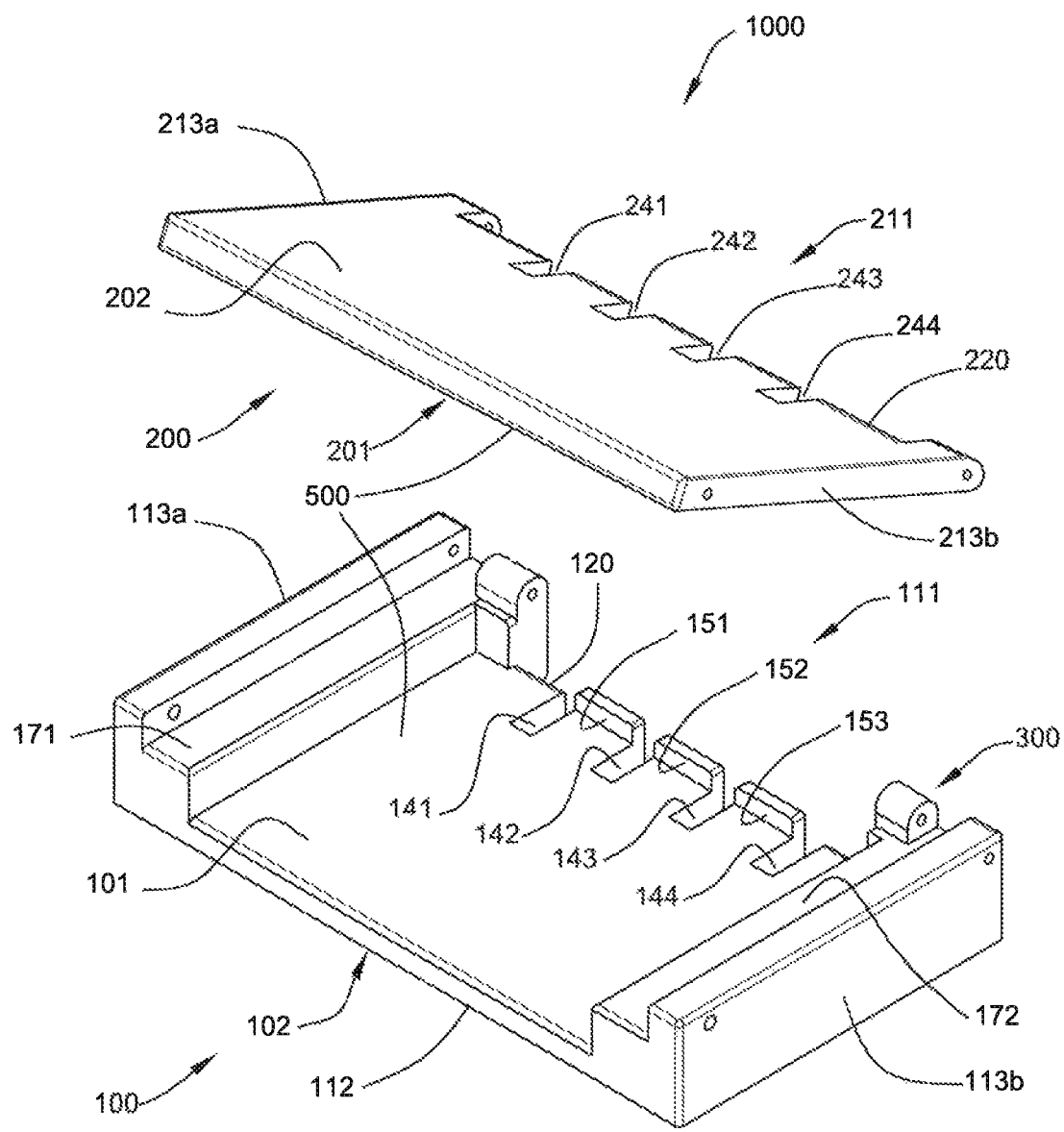
FIG. 2 illustrates an exploded view of a sealing jig for use in an embodiment of a method for sealing the bag shown in FIG. 1, wherein the jig has a first plate and a second plate wherein the plates are hinged together in a generally "clamshell" type arrangement.

FIG. 2 shows an illustrative sealing jig (in an exploded view) for use in an embodiment of a method for sealing the bag shown in FIG. 1. Illustrated jig 1000 has first panel 100 having an inside surface 101 and an outside surface 102, a first end 111, a second end 112, and side ends 113a, 113b, and a plurality of cut outs (four cut outs are illustrated; 141, 142, 143, 144) arranged in the first end 111, and a second panel 200 having an inside surface 201 and an outside surface 202, a first end 211, a second end 212, and side ends 213a, 213b, and a plurality of cut outs (four cut outs are illustrated; 241, 242, 243, 244) arranged in the first end 211, the inside surfaces of the first and second panels forming an interior 500 of the jig. The first end 111 of the first panel 100 also includes a plurality of lips (three lips are illustrated; 151, 152, 153) on an edge 120 of the end, the lips projecting upwardly, wherein the lips are arranged on the edge between the cutouts. The first end 211 of the second panel 200 also includes an edge 220.

The illustrated jig also has the plates hinged together (via hinge 300) in a generally "clamshell" type arrangement. Additionally, the illustrated first plate is wider than the illustrated second plate, and the first plate has a step arrangement 171, 172 at each side, such that sides of the second plate fit in the step arrangement at each side of the first plate.

In accordance with an embodiment of the method according to the invention the jig 1000 is opened, and the freezing bag 50 is placed in the interior 500 of the jig 1000. Typically, the bag is placed on the inside surface 101 of the first panel 100, but the bag can be placed on the inside surface 201 of the second panel 200. The jig is subsequently closed, such that the inside surfaces 101, 201 of the first and second panels contact the exterior surfaces 12, 22 of the bag's side walls 10, 20, and a surface of the lips 151-153 contacts the end 220 of the second panel.

Energy, preferably heat, is applied to the bag through the cut outs, sealing the passageway 75 (at 75a, 75b, 75c, and 75d), and, after removal from the jig, heat is also applied to the bag and fill line tubing to seal at 75e and to provide the desired number of segments (usually, in the range of about 2 to about 6 segments).

The following example further illustrates the invention but, of course, should not be construed as in any way limiting its scope.

EXAMPLE

This example demonstrates a method of sealing a multiple chamber bag in accordance with an embodiment of the invention.

A five chamber blow molded EVA freezable bag as generally illustrated in FIG. 1 is obtained. The open end of each chamber is closed by an EVA spike entry port that is radio frequency welded into position and overwrapped with EVA material.

A transfer bag containing biological fluid cord blood mixed with DMSO is connected to the transfer fill line of the freezable bag via sterile docking (a clamp is associated with the transfer line). With the freezable bag held above the transfer bag, the freezable bag is rolled to compress the bag and express air into the transfer bag. After the air is expressed from the freezable bag, the transfer bag is held above the freezing bag, and the biological fluid is passed from the transfer bag, and into the chambers to provide about 4 mL of fluid in each chamber. As some air is present in the freezable bag, as much as possible is removed (by "burping" the bag) before clamping the line between the transfer bag and the freezable bag. Sufficient fluid remains in the transfer fill line to provide the desired number of segments. The transfer fill line is cut and sealed at the cut end via sterile docking.

The bag is placed in a jig, wherein the jig is as generally shown in FIG. 2. The jig is closed and heat is applied to the bag at each cut out (using a heatable tip that clamps the bag on either side of the passageway), starting with the passageway furthest from the fill line, and working toward the fill line (sealing, in order, 75a, 75b, 75c, and 75d). The bag is removed from the jig, and heat is also applied to the bag and fill line tubing to seal at 75e and along the tubing to provide 6 segments.

The bag, having 5 sealed and fluidly isolated biological fluid containing compartments, each compartment containing about the same volume of biological fluid (about 4 mL±0.2 mL), is frozen.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for sealing a freezing bag having multiple compartments containing biological fluid, the method comprising:
    providing a freezing bag comprising opposing side walls having exterior surfaces, a top, and a bottom, and multiple compartments, each compartment having an interior volume containing biological fluid therein, the bag further comprising a passageway providing fluid communication between the compartments,
    inserting the freezing bag between first and second panels of an open jig, the first and second panels each having an outside surface and an inside surface, the inside surfaces forming an interior of the jig, the first and second panels each having a plurality of cut outs at one end of the panels;
    closing the jig with the bag located in the interior of the jig, such that the inside surfaces of the first and second panels contact the exterior surfaces of the opposing side walls of the bag; and
    applying heat to the bag through the plurality of cut outs;
    wherein applying heat seals the passageway at multiple locations and forms a plurality of sealed fluidly isolated biological fluid containing compartments in the bag, each compartment containing about the same volume of biological fluid.

2. The method of claim 1, wherein the panels are connected by a hinge, and closing the jig comprises pivoting one of the first or second panels toward the other of the first or second panels.

3. The method of claim 2, comprising forming at least 3 sealed fluidly isolated biological fluid containing compartments in the bag, each compartment containing about the same volume of biological fluid.

4. The method of claim 3, further comprising freezing the freezing bag comprising the plurality of sealed fluidly isolated biological fluid containing compartments.

5. The method of claim 2, further comprising freezing the freezing bag comprising the plurality of sealed fluidly isolated biological fluid containing compartments.

6. The method of claim 1, comprising forming at least 3 sealed fluidly isolated biological fluid containing compartments in the bag, each compartment containing about the same volume of biological fluid.

7. The method of claim 6, further comprising freezing the freezing bag comprising the plurality of sealed fluidly isolated biological fluid containing compartments.

8. The method of claim 1, further comprising freezing the freezing bag comprising the plurality of sealed fluidly isolated biological fluid containing compartments.

* * * * *